United States Patent
Koch et al.

(10) Patent No.: US 6,936,661 B2
(45) Date of Patent: Aug. 30, 2005

(54) MEDICAL CONTACT ADHESIVE COMPRISING A TWO PHASE ADHESIVE MATRIX OF POLYACRYLATES AND POLYAMINE SALTS

(75) Inventors: Andreas Koch, Melsbach (DE); Stefan Bracht, Ochtendung (DE); Christoph Schmitz, Rheinbrohl (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 10/333,783

(22) PCT Filed: Jul. 11, 2001

(86) PCT No.: PCT/EP01/07982

§ 371 (c)(1),
(2), (4) Date: Jul. 21, 2003

(87) PCT Pub. No.: WO02/08352

PCT Pub. Date: Jan. 31, 2002

(65) Prior Publication Data

US 2004/0010054 A1 Jan. 15, 2004

(30) Foreign Application Priority Data

Jul. 24, 2000 (DE) .......................................... 100 35 891

(51) Int. Cl.⁷ .............................................. C08L 33/02
(52) U.S. Cl. ....................... 525/221; 525/222; 525/227; 525/228; 525/230; 428/352; 428/355 AC; 428/355 CN

(58) Field of Search .................................. 525/221–222, 525/227–228, 230, 352, 355 CN, 355 AC

(56) References Cited

U.S. PATENT DOCUMENTS 5,977,242 A    11/1999    Origuchi et al. ............ 524/521

FOREIGN PATENT DOCUMENTS

DE          44 29 791 A1       8/1994
DE          199 18 105 C1      9/2000

OTHER PUBLICATIONS

Database WPI Section Ch, Week 199506, Derwent Publications LTd., London GB; XP002183812 & JP 06 322342 A (Konishi Co Ltd), Nov. 22, 1994

*Primary Examiner*—Peter Szekely
(74) *Attorney, Agent, or Firm*—Birch, Stewart, Kolasch & Birch, LLP

(57) ABSTRACT

A medical pressure sensitive adhesive based on polyacrylates and neutral polyamine salts is characterized in that it has a pressure-sensitive adhesive matrix of two polymer components A and B, with polymer component A being a polyacrylate pressure-sensitive adhesive containing carboxyl groups, the carboxyl groups of which are neutralized; the polymer component B being a neutral polyamine salt obtained by reacting a polyacrylate copolymer containing amino groups with an acid, with the polymer component B being dispersed in the polymer component A, and the two components forming a two-phase system.

21 Claims, 1 Drawing Sheet

MEDICAL CONTACT ADHESIVE COMPRISING A TWO PHASE ADHESIVE MATRIX OF POLYACRYLATES AND POLYAMINE SALTS

This application is the national phase under 35 U.S.C. § 371 of PCT International Application No. PCT/EP01/07982 which has an International filing date of Jul. 11, 2001, which designated the United States of America.

This application claims priority under 35 U.S.C. §119 of German application no. 100 35 891.8, filed Jul. 24, 2000, the entire contents of which is hereby incorporated herein by reference.

BACKGROUND OF THE INVENTION

1. Field of the Invention

The present invention relates to polyacrylate-based pressure-sensitive adhesives for medical purposes which are used in the production of adhesive plasters, transdermal therapeutic systems (TTSs) and other devices adhering to the skin. The invention especially relates to active substance-containing pressure sensitive adhesives for use in transdermal therapeutic systems. The invention furthermore comprises the use of such pressure sensitive adhesives for the production of devices which, for therapeutic or diagnostic purposes, are durably secured to the skin.

2. Description of the Related Art

Pressure sensitive adhesives are highly viscous, elastic adhesives which, after one has exerted a short, slight pressure thereon, immediately and durably adhere to the substrate concerned, e.g. the skin. It is for this reason that they are called "pressure sensitive" adhesives (=PSA). On account of their viscoelasticity they are capable of conforming very well to the skin of different areas of the body and are therefore suited to a multitude of medical application purposes. In addition they can in most cases be removed again from the substrate at a later point in time, without thereby destructing the substrate. In transdermal therapeutic systems, pressure sensitive adhesives can have both the function of an active substance reservoir in the form of a polymer matrix, into which the active substance has been introduced, and the function of the pressure-sensitive adhesive attachment of the systems on the skin.

The presently most frequently utilised pressure sensitive adhesives are based on synthetic rubber polymers, polyacrylates or silicones. Pressure sensitive adhesives based on synthetic rubber polymers generally require the use of so-called "tackifiers", e.g. tackifying resins based on colophony derivatives, to be able to achieve a sufficient bioadhesive adhesion to the human skin. By contrast thereto, pressure-sensitive adhesives based on polyacrylate polymers or silicones are—because of their chemical structure and the physicochemical properties resulting therefrom—self-adhesive without the necessity of adding tackifying substances.

With pressure sensitive adhesives based on synthetic rubber polymers and tackifying resins, it is frequently observed that they possess, insufficient skin tolerance, whereas the problem of skin tolerance in polyacrylate or silicone pressure sensitive adhesives has for the most part been solved.

However, the presently known polyacrylate polymers and silicones do not meet all of the demands made on medical high-performance adhesives, for instance for use in transdermal therapeutic systems. Above all, it is to be emphasized in this respect that the adhesion of the pressure sensitive adhesive to the skin must be maintained even under extreme conditions, for instance in extreme climatic conditions or in the case of increased and enduring moistness of the skin, e.g. caused by sweating heavily. Increased formation of skin moisture can also be brought about by the occlusion effect caused by a TTS applied to the skin.

In addition, in particular for silicone adhesives, there has as yet no satisfactory solution been found to the problem of "cold flow". With respect to TTSs or pressure sensitive adhesive plasters, this term is understood to refer to punched plaster surfaces flowing in lateral directions at their edges of cut, which flowing is due to insufficient cohesion. This can lead to great problems especially in the ultimate stages of the production, for example due to the pressure sensitive matrix becoming irreversibly stuck to the packaging material. A further unwanted effect of "cold flow" consists in the pressure sensitive adhesive, when applied to the skin, entering more deeply into the pores of the skin than is desired, which makes the later removal of the plaster or the TTS more difficult, or painful.

Pressure-sensitive adhesives based on polyacrylate polymers frequently involve the problem of requiring the addition of adhesive power modulators, e.g. of so-called plasticizers, in order to be able to ensure a sufficient adhesive effect even under the above-described extreme conditions. To this end, the pressure sensitive polyacrylate adhesives must be adjusted to be very soft, with the consequence that it is often unavoidable that residues of adhesive remain on the skin after the plaster has been removed.

Especially in the case of pressure sensitive adhesives containing acidic polyacrylates, further problems result from the fact that they possess a poor tolerance to moisture, which entails drawbacks in respect of adherence to the skin, and from the fact that they possess a chemical affinity to basic active agents. The latter is disadvantageous since as a result of an irreversible acid-base reaction between the acid polyacrylates and the basic active substances, the release and thereby the bioavailability of the pharmaceutical agent in question is reduced.

For this reason, for a pressure-sensitive adhesive to be suitable for use in transdermal therapeutic systems, it should ideally be compatible, in physicochemical respects, with the most varied pharmaceutical active substances and should not enter into unfavourable interactions with those substances.

Furthermore, a pressure sensitive adhesive should possess the following advantageous adhesive properties: it should have a certain minimum tackiness without requiring the addition of a plasticizer. This minimum tackiness should change into an aggressive tackiness only upon exposure to skin moisture, but the adhesive should nevertheless be water-resistant. A further requirement is that after the application has ended, it should be possible to remove the adhesive from the skin without leaving any residues.

In DE 44 29 791 A1 there is described a pressure sensitive adhesive composition containing two polymer components, namely a self-adhesive, carboxyl group-containing polyacrylate polymer and a basic, amino group-containing polymer. In this way, cross-linking is to be brought about by interactions between the acid and the basic groups. Under the influence of skin moisture, these interactions are weakened, which results in a desired increase in tackiness for the duration of the application. However, the initial tackiness of such a pressure sensitive adhesive is very poor, which is why plasticizers have to be added to achieve the required minimum or base tackiness. The added tackifiers can, however, lead to the above-described drawbacks. Since the above described interaction between the acid and the basic groups is reversible under the influence of moisture, there may occur unwanted interactions with the possibly present acid or basic active agents if the adhesive is used in a TTS, this will lead to disadvantageous effects on the release of the active agents to the skin and thereby on their bioavailability.

It has furthermore been proposed to neutralise acid pressure-sensitive polyacrylate adhesives with alkali metal compounds in order to improve their adhesive properties, but only in connection with acid pharmaceutical active substances. By way of the neutralisation of the acid pressure-sensitive polyacrylate adhesives it is intended to achieve an increase in coherence, improved adhesion to the skin, increased loadability with plasticizing auxiliary substances, as well as increased resistance to moisture. Such pressure sensitive adhesives do, however, have the disadvantage of being little suited as active substance reservoirs for, for instance, hydrolysis-sensitive or chemically unstable pharmaceutical active agents since the slightly alkaline medium of these pressure-sensitive adhesive systems entails the risk of accelerated decomposition, respectively of an increased break-down of the active substances. In addition, neutralised polyacrylate polymers, contrary to expectations, proved in part to be moisture-sensitive and diminishing in their adhesive power, the latter being due to their strong cohesion and the poor flowability associated therewith.

For this reason, in the case of pressure-sensitive adhesive systems based on neutralised polyacrylates, it is necessary to add highly water-binding additives to increase the moisture tolerance. Moreover, it is necessary to use plasticizers to achieve an optimal skin adhesion, or to add an additional pressure-sensitive adhesive layer improving the bond of the system with the skin.

SUMMARY OF THE INVENTION

It was thus the object of the present invention to provide medical pressure-sensitive adhesives which are suitable for the use in the afore-mentioned application fields, especially for the use in transdermal therapeutic systems, and which do not tend towards "cold flow" during manufacture and storage, which possess sufficiently pressure-sensitive skin adhesion and good initial tackiness;

whose skin adhesion is maintained for the entire duration of application, or even increases, under the influence of skin moisture, which, on account of their water or moisture resistance can be removed from the skin without residues when the therapy has ended, i.e. without leaving residues of adhesive, and which are chemically inert or compatible with acid or basic pharmaceutical active substances, and, in particular, do not enter into interactions, for instance by salt formation or formation of hydrogen bridges.

Surprisingly, this object is achieved by a pressure sensitive adhesive according to the invention. This is unexpected first of all because neutral polyamine salts (component B) have a water absorption capacity and swelling capacity which is too high, and as such appear not to be suitable for use as pressure sensitive adhesives since these properties deteriorate their adhesive power and interfere with the release, in particular of hydrophilic active agents, from such an adhesive matrix. It is not possible to remove such adhesives from the skin without leaving residues.

DETAILED DESCRIPTION

Figure 1:
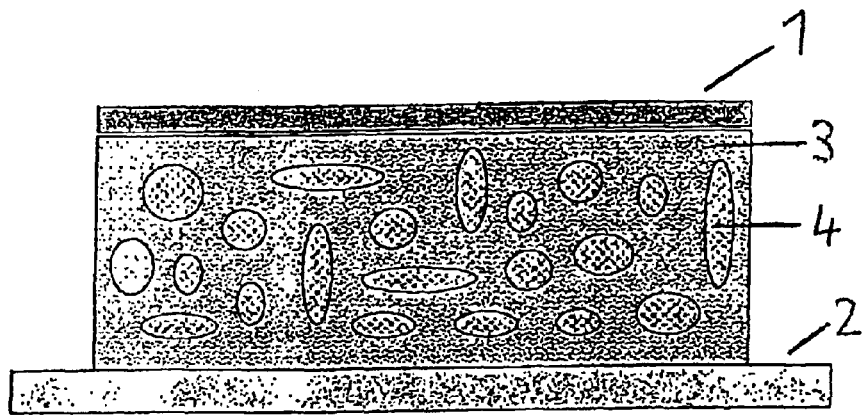
FIG. 1 shows a schematic representation of a two phase TTS pressure-sensitive adhesive matrix.

The pressure-sensitive adhesive of the invention has an adhesive matrix comprising a combination of two polymer components, which are designated as polymer components A and B. Polymer component A is a carboxyl groups-containing polyacrylate pressure-sensitive adhesive, whose carboxyl groups are neutralised. For this purpose, a pressure-sensitive polyacrylate adhesive is preferred which contains at least 3 mole percent of acrylic or methacrylic acid polymerized therein. The neutralisation of the carboxyl groups is preferably brought about by alkali lyes.

Polymer component B is a neutral polyamine salt obtained by reacting an amino groups-containing polyacrylate copolymer with an acid. Preferably, the amino groups-containing polyacrylate is a poly(meth)acrylate copolymer of neutral methacrylic acid esters and dimthylaminoethyl methacrylate (e.g. Eudragit E 100, by Röhm).

Preferred acids for the reaction with the amino groups-containing polyacrylate, respectively the amino groups-containing poly(meth)acrylate copolymer, are fatty acids and/or dicarboxylic acids, it also being possible to use a mixture of acids. Preferred fatty acids are unsaturated fatty acids, especially preferred are those having a chain length of 6 to 20 C atoms. Preferred dicarboxylic acids are saturated dicarboxylic acids with 4 to 10 C atoms.

The adhesive matrix formed by the two components is a two-phase system in which the polymer component B is dispersed in the polymer component A, similarly to a water-in-oil emulsion. This is due to the fact that the polymer component A is water-insoluble while polymer component B (polyamine salt) is water-soluble. The quaternary polymethacrylate (polyamine salt) is hydrophilic and ionic, and thus highly water-soluble.

Polymer component B is dispersed in component A, resulting in the formation of regions that can be regarded as "micro-reservoirs". If the pressure sensitive adhesive of the invention is, as provided for, loaded with active substance in both components, the active substance spreads between component A and the micro-reservoirs B, which are dispersed in the polymer component A. The distribution of the active substance between the two polymer components takes place in accordance with the distribution coefficient of the pharmaceutical active agent in question, for example with respect to the system octanol/water.

The two polymer components may be mixed or dispersed in different parts by weight to obtain the above mentioned two-phase system. In this respect, a ratio of the component A to the component B of 0.5:1 to 50:1, relative to the parts by weight, is preferred. Especially preferred is a ratio of 1:1 to 10:1.

A further advantage of the medical pressure sensitive adhesives of the invention resides in the fact that the use of plasticizers, which is otherwise common for technological reasons, can be dispensed with.

The adhesive system proposed according to the invention exhibits excellent skin adhesion properties, even under the most difficult conditions, and shows no "cold flow". Furthermore, when the duration of application has terminated, a plaster or a TTS which is provided with the pressure sensitive adhesive of the present invention can be removed from the skin without leaving any residues whatsoever. Compared to pressure sensitive adhesives made exclusively on the basis of polyacrylates or polyamine salts, a pressure sensitive adhesive of the present invention also has better release properties for the active substances dissolved or dispersed therein (see FIG. 2). A further advantage of the pressure sensitive adhesives according to the invention consists in that in the manufacture thereof it is possible to use polyacrylates as starting materials which are already well known and commercially available in pharmaceutical technology and which are approved by The FDA (see Example 1).

As mentioned, the medical pressure sensitive adhesive according to the present invention can be loaded with pharmaceutically active substances, so that at least one of the two polymer components contains active substance. The achievable load capacity is comparable with that of polyacrylate polymers of the state of the start. However, with the pressure-sensitive adhesives of the present invention, it is possible to dispense with the otherwise required solubilizers for the active substance, whose function can be taken over by plasticizers.

Preferably, the two polymer components A and B contain the same pharmaceutical active substance. In special cases, it may also be of advantage to load component A and component B with different active substances.

An additional crosslinking of the polyacrylate polymer backbone, to prevent "cold flow", is not necessary with the pressure-sensitive adhesives according to the present invention. If desired, such crosslinking can be accomplished by adding metal chelates, e.g. aluminium acetyl acetonate.

To improve the skin permeation of the active substances introduced into the pressure sensitive adhesive matrix of a TTS, so-called penetration enhancers may be added to the medical pressure sensitive adhesive according to the invention forming the pressure-sensitive adhesive matrix of the TTS; such penetration enhancers are, for instance, saturated or unsaturated fatty acids, straight-chain or branched fatty alcohols or esters thereof, polyhydric aliphatic alcohols or polyethylene glycols, sorbitane fatty acid esters and the derivatives thereof obtained by ethoxylation, or fatty alcohol ethoxylates.

The portion of these penetration enhancers is preferably 5–20%-wt.

In case of doubt, all indications referring to portions in percent by weight refer to the weight of the pressure-sensitive adhesive after removing the solvents added during manufacture.

In an especially preferred embodiment, the medical pressure sensitive adhesive contains 60–95%-wt of a two-phase, neutralised pressure sensitive adhesive, and 1–20%-wt of an active substance present in the said two-phase pressure sensitive adhesive in dissolved or dispersed form. The polymer component A of the two-phase pressure sensitive adhesive here is a neutralised polyacrylate copolymer having at least 3 mole percent acrylic or methacrylic acid polymerised therein, and polymer component B of the two-phase pressure sensitive adhesive is a neutral polyamine salt obtained by reacting a poly(meth)acrylate copolymer of neutral methacrylic acid esters and dimethylaminoethyl methacrylate.

Such an active substance-containing medical pressure sensitive adhesive is preferably suitable as an active substance matrix of a transdermal therapeutic system.

Preferably used as active substances with which the medical pressure sensitive adhesives according to the present invention can be loaded and which subsequently, during application to the skin of a patient, can be released are acid and/or basic pharmaceutically active substances, or their pharmaceutically acceptable salts.

"Basic pharmaceutically active substances" is understood to mean those pharmaceutically active substances which in their molecular structure have at least one group which can react chemically as a Lewis base. Preferably, such groups posses an aliphatic or aromatic primary, secondary or tertiary amine function. Examples are naturally occurring alkaloids such as atropine, scopolamine, physostigmine, galanthamine, pilocarpine, morphine or ergotamine, or synthetically produced active agents such as apomorphine, moxonidine, desoxypeganine, buprenorphine, salbutamol or clonidine.

"Acid pharmaceutically active substances" is understood to mean those pharmaceutically active substances which in their molecular structure possess at least one group which can react chemically as a Lewis acid. Preferably, such groups have an acidic carbonyl function. Examples are the carboxylic acids acetylsalicylic acid, dehydrocholic acid, ketoprofene, lovastatine and fluorobiprofene. However, apart from acid or basic active substances, other active substances which are suitable for transdermal administration can be incorporated in the medical pressure sensitive adhesives of the present invention in order to produce active substance matrices for transdermal therapeutic systems.

The medical pressure sensitive adhesives according to the present invention can be utilized wherever good and reliable adhesion to the skin for a prolonged period of time is required. They are therefore especially suited for the manufacture of adhesive dressings, fixing plasters, adhesive plasters, wound plasters or self-adhesive electrodes. These pressure sensitive adhesives can be used with particular advantage for making transdermal therapeutic systems in plaster form for the transdermal administration of pharmaceutically active substances. The structure of such a TTS is schematically represented in FIG. 1.

The medical pressure sensitive adhesives according to the present invention and their advantageous properties will in the following be explained by means of examples and drawings.

EXAMPLE 1

Preparation of a self-adhesive, active substance-containing pressure sensitive adhesive film:

Component A:

An acid polyacrylate adhesive containing free carboxyl groups (e.g. Durotak® 387–2051; in ethyl acetate/n-heptane; 52%-wt; by National Starch) is neutralised according to its strong acid number of 37–44 mg KOH per g dry weight with a 10% (percent by weight) ethanolic or methanolic solution of sodium or potassium hydroxide by adding the solution while stirring. The viscosity increase occurring in the process can be compensated by addition of solvents (ethyl acetate/n-heptane/methanol). To the neutralised acrylate adhesive material thus obtained there may optionally be added aluminium acetyl acetonate (4%-wt in ethyl acetate) as crosslinker in a concentration range of 0.005 to 0.5%-wt, relative to aluminium.

Component B:

Eudragit® E 100 (by Röhm; 15.9 parts by weight, corresponding to 57%-wt) is dissolved in ethanol and is converted with fatty acids to a polyamine salt, the said acids being added while stirring. Suitable fatty acids are, for example, lauric acid (9.4 parts, corresponding to 33.5%-wt) and adipic acid (1.86 parts, corresponding to 6.6%-wt).

The components A and B thus obtained are mixed at a ratio of 1:1 (relative to the solids weight) and homogenised by stirring. In 13.03 g of the 29.5% premixed polyacrylate/polyamine salt adhesive solution are introduced, in portions, 0.665 g of morphine benzoate (13.1%-wt) as active substance, and 0.5 g of oleic acid as enhancer. For the purpose of lowering the viscosity of the preparation, methanol can be added. The preparation is homogenised for a total of 30 min at a stirring velocity of 350 rpm. This is followed by degassing for a quarter of an hour at 45° C. in an ultrasound bath, in order to remove excess air from the material.

Then, the active substance-containing adhesive solution is spread with the aid of a doctor knife in a wet-layer thickness of 300 μm on a siliconised-polyethylene terephthalate film. Thereafter, the solvents are removed by drying for half an hour at 50° C. in a drying cupboard with waste air guidance. The solvent-free, active substance-containing adhesive film is subsequently covered with a 15-μm-thick polyester film by laminating. The adhesive portion in the laminate, after completed fabrication, amounts to 76.9%-wt. The laminate has the basic structure of a two-phase TTS pressure-sensitive adhesive matrix, as schematically represented in FIG. 1.

FIG. 1 shows, in cross-section, the schematic structure of a TTS with a two-phase pressure-sensitive adhesive matrix according to the invention as active substance reservoir. The individual components of the TTS are designated as follows:

(1) active substance-impermeable backing layer;
(2) detachable protective layer (or "release liner");
(3) self-adhesive polyacrylate matrix (neutralised carboxyl group-containing polyacrylate pressure-sensitive adhesive; component A), with active substance;
(4) poly(meth)acrylate (neutral polyamine salt; component B) dispersed therein, likewise with active substance. The dispersed poly(meth)acrylate forms "micro-reservoirs".

The structure of a TTS represented here is merely to serve as an example. The invention also extends to variants of embodiments of TTSs which divert from the structure shown.

Materials suitable for the backing layer are above all polyesters which are characterized by a particular strength, such as polyethylene terephthalate and polybutylene terephthalate, but in addition almost any other skin-tolerable plastics, such as polyvinyl chloride, ethylenevinyl acetate copolymers, polyvinyl acetate, polyethylene, polypropylene, polyurethane, cellulose derivatives, and many more. In the individual case, the backing layer may be provided with an additional layer thereon, e.g. by vacuum metallizing, especially of aluminium.

Basically, the same materials can be used for the detachable protective layer as are used for the backing layer, provided that they are rendered detachable by a suitable surface treatment such as siliconization. However, other detachable protective layers such as polytetrafluoroethylene-treated paper or cellophane® (cellulose hydrate) may be used as well.

EXAMPLE 2

In accordance with the procedure described in Example 1, a pressure-sensitive adhesive according to the invention with a polymer content of 86.9%-wt and an active substance content of 13.1%-wt was prepared. The pressure sensitive adhesive consists, as described under Example 1, of Durotak® 387–2051 (neutralised) and neutral polyamine salts (Eudragit® E 100, salified with lauric and adipic acid). As active substance, morphine benzoate was used.

With this active substance-containing pressure-sensitive adhesive matrix (short designation: "polyacrylate/polymethacrylate TTS") the active substance permeation was examined in an in-vitro skin model (human full-thickness skin, female breast, age: 23 years). As acceptor medium, 0.9% NaCl solution (with 0.1%-wt of NaN$_3$) was used. The temperature was 37° C. for the duration of the release experiment.

Figure 2:
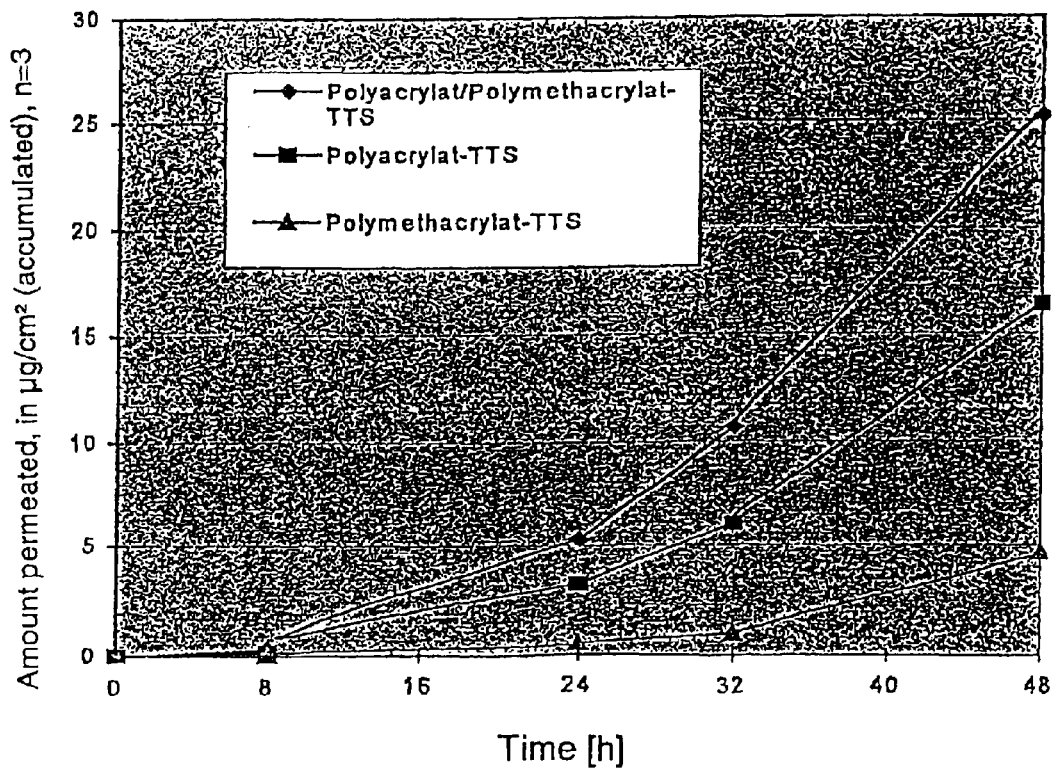
FIG. 2 shows a graph of permeation results as a function of time.

The permeation values measured are graphically represented in FIG. 2.

As comparison examples, the following pressure sensitive adhesive matrices were prepared, which likewise contained 13.1%-wt. active substance (morphine benzoate):

a) pressure sensitive adhesive matrix with 61.9%-wt of acid Durotak® 387–2051 pressure-sensitive adhesive (not neutralised) and 25%-wt of oleic acid; short designation: "polyacrylate TTS"

b) pressure sensitive adhesive matrix with 86.9%-wt of neutral polyamine salt pressure sensitive adhesive (Eudragit® E 100, salified with lauric and adipic acid); short designation: "polymethacrylate TTS".

Using the pressure sensitive adhesive matrices "polyacrylate TTSs" and "polymethacrylate TTSs" as comparison examples, the active substance permeation on human full-thickness skin was examined as described above. The results of these permeation experiments are likewise shown in FIG. 2.

It turned out that using the pressure sensitive adhesive ("polyacrylate/polymethacrylate TTS") a clearly improved skin permeation was achieved, as compared to the comparative examples.

Since the pressure sensitive adhesives according to the present invention not only stand out for their increased active substance release, but also for their improved adhesive characteristics, they excellently meet the demands made on a medical pressure sensitive adhesive.

What is claimed is:

1. Medical pressure sensitive adhesive based on polyacrylates and neutral polyamine salts, which comprises a pressure-sensitive adhesive matrix of two polymer components A and B, with polymer component A being a polyacrylate pressure-sensitive adhesive containing carboxyl groups, the carboxyl groups of which are neutralised; and polymer component B being a neutral polyamine salt obtained by reacting a polyacrylate copolymer containing amino groups with an acid selected from the group consisting of fatty acids and dicarboxylic acids, or with a mixture of at least two acids selected from the group consisting of fatty acids and dicarboxylic acids, wherein the polymer component B being dispersed in the polymer component A, and the two components form a two-phase system.

2. The pressure sensitive adhesive according to claim 1, wherein the acid for reacting the amino groups-containing polyacrylate copolymer is selected from the group consisting of an unsaturated fatty acid, a mixture of two or more unsaturated fatty acids, a dicarboxylic acid, a mixture of two or more dicarboxylic acids and a mixture of at least one unsaturated fatty acid with at least one dicarboxylic acid.

3. The pressure sensitive adhesive according to claim 1, wherein the amino groups-containing polyacrylate is a poly(meth)acrylate copolymer of neutral methacrylic acid esters and dimethylaminoethyl methacrylate.

4. The pressure sensitive adhesive according to claim 1, wherein the carboxyl groups-containing polyacrylate adhesive contains at least 3 mole percent of acrylic or methacrylic acid polymerised therein.

5. The pressure sensitive adhesive according to claim 1, wherein the carboxyl groups of the polyacrylate pressure sensitive adhesive are neutralised with alkali lyes.

6. The pressure sensitive adhesive according to claim 1, wherein the components A and B are dispersed at a ratio of 0.5:1 to 50:1, by weight.

7. The pressure sensitive adhesive according to claim 1, wherein the neutralised, carboxyl groups-containing polyacrylate adhesive is crosslinked by addition of metal chelates.

8. The pressure sensitive adhesive according to claim 1, wherein at least one of the two polymer components contains one or more active substances, with the active substance(s) being present in the polymer components in dissolved or suspended form.

9. The pressure sensitive adhesive according to claim 8, that comprises:
   60–95%-wt of the two-phase, neutralised pressure sensitive adhesive—with the polymer component A being a neutralised polyacrylate copolymer with at least 3 mole percent of acrylic or methacrylic acid polymerised therein, and with the polymer component B being a neutral polyamine salt obtained by converting a poly (meth)acrylate copolymer of neutral methacrylic acid esters and dimethylaminoethyl methacrylate; and
   1–20%-wt of at least one active substance, present in the two-phase pressure-sensitive adhesive in dissolved or dispersed form.

10. The pressure sensitive adhesive according to claim 8, wherein the adhesive contains one or more penetration-enhancing additives which are dissolved or suspended in the polymer components.

11. A transdermal therapeutic system comprising a plaster having an active substance-impermeable backing layer, an active substance-containing reservoir comprising a polymer matrix and a detachable protective layer, wherein the active substance-containing reservoir contains a pressure sensitive adhesive according to claim 1.

12. The pressure sensitive adhesive according to claim 1, wherein the carboxyl goups of the polyacrylate pressure sensitive adhesive are neutralized with NaOH or KOH.

13. An article comprising a pressure sensitive adhesive according to claim 1, said article further comprising an adhesive dressing, a fixing plaster, an adhesive plaster, a wound plaster or a self-adhesive electrode.

14. A process for preparing a pressure sensitve adhesive, comprising:
   preparing a polymer A by neutralizing an acidic polyacrylic adhesive containing free carboxyl groups;
   preparing a polymer component B by reacting an amino group-containing polyacrylate copolymer with an acid selected from the group consisting of fatty acids and dicarboxylic acids, or with a mixture of at least two acids selected from the group consisting of fatty acids and dicarboxylic acids; and
   dispersing said polymer component B in said polymer component A to obtain a two-phase system.

15. The process according to claim 14, wherein at least one active substance is added to at least one of said polymer components A or B.

16. The process according to claim 15, wherein the active substance is selected from the group consisting of acid pharmaceutically active substances, pharmaceutically acceptable salts of said acid pharmaceutically active substances, basic pharmaceutically active substances and pharmaceutically acceptable salts of said basic pharmaceutically active substances.

17. The process according to claim 15, wherein said adhesive is further formed using the steps of:
   spreading the active subtance-containing pressure sensitive adhesive in the form of a layer onto a substrate; and
   drying said layer to thereby obtain an active substance-containing film.

18. The pressure sensitive adhesive according to claim 1, wherein the components A and B are dispersed at a ratio of 1:1 to 10:1, by weight.

19. The pressure sensitive adhesive according to claim 1, wherein the neutralised, carboxyl groups-containing polyacrylate adhesive is crosslinked by addition of aluminum acetyl acetonate.

20. The pressure sensitive adhesive according to claim 1, wherein both polymer components contain at least one active substance, with the active substance(s) being present in the polymer components in dissolved or suspended form.

21. The pressure sensitive adhesive according to claim 10, wherein the adhesive contains 5–20%-wt of said penetration enhancer.

* * * * *